(12) United States Patent
Ishikawa et al.

(10) Patent No.: US 9,993,157 B2
(45) Date of Patent: Jun. 12, 2018

(54) OPTICAL MEASURING SYSTEM

(75) Inventors: Akihiro Ishikawa, Kyoto (JP);
Yoshihiro Inoue, Kyoto (JP); Takashi Amita, Kyoto (JP); Satoru Kohno, Fuchu (JP); Haruhide Udagawa, Kyoto (JP); Yoshinori Masuda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 599 days.

(21) Appl. No.: 14/390,728

(22) PCT Filed: Apr. 5, 2012

(86) PCT No.: PCT/JP2012/059324
§ 371 (c)(1),
(2), (4) Date: Oct. 22, 2014

(87) PCT Pub. No.: WO2013/150629
PCT Pub. Date: Oct. 10, 2013

(65) Prior Publication Data
US 2015/0080739 A1    Mar. 19, 2015

(51) Int. Cl.
*A61B 6/00* (2006.01)
*A61B 5/00* (2006.01)
*A61B 5/1455* (2006.01)

(52) U.S. Cl.
CPC .......... *A61B 5/0042* (2013.01); *A61B 5/0075* (2013.01); *A61B 5/0082* (2013.01);
(Continued)

(58) Field of Classification Search
CPC .................................................. A61B 5/0059
(Continued)

(56) References Cited

U.S. PATENT DOCUMENTS

| 2008/0073128 | A1  | 3/2008  | Umemoto |
| 2008/0183056 | A1* | 7/2008  | Atsumori ............ A61B 5/0059 600/310 |
| 2011/0290965 | A1* | 12/2011 | Virgin .................. A47G 1/1606 248/205.3 |

FOREIGN PATENT DOCUMENTS

| JP | 2001-337033 A | 7/2001 |
| JP | 2002-143169 A | 5/2002 |

(Continued)

OTHER PUBLICATIONS

Gary Strangman et al., "Factors affecting the accuracy of near-infrared spectroscopy concentration calculations for focal changes in oxygenation parameters", NeuroImage 18 (2003) 865-879.
(Continued)

*Primary Examiner* — Amanda Patton
*Assistant Examiner* — Philip C Edwards
(74) *Attorney, Agent, or Firm* — McDermott Will & Emery LLP

(57) ABSTRACT

An optical measuring system comprises a control device and an optical meter. The optical meter comprises a first case, a first controller for controlling light emitters for irradiating a patient with light and light receivers for receiving light from the patient to obtain measurement data regarding a cerebral activity, and a first transmitter and receiver for transmitting the measurement data to the control device. The control device comprises a second case removably attached to the first case, a display and input device on a surface of the second case, a second transmitter and receiver for receiving the measurement data from the optical meter, and a second controller for controlling the display and input device to display the measurement data from the optical meter. The second case can be attached on a top face of the first case when the first case is placed on a table.

8 Claims, 12 Drawing Sheets

(52) U.S. Cl.
CPC ........ *A61B 5/14553* (2013.01); *A61B 5/4064* (2013.01); *A61B 5/742* (2013.01); *A61B 5/7475* (2013.01); *A61B 2562/046* (2013.01)

(58) Field of Classification Search
USPC ................................................ 600/476, 310
See application file for complete search history.

(56) References Cited

FOREIGN PATENT DOCUMENTS

| | | |
|---|---|---|
| JP | 2005-334049 A | 12/2005 |
| JP | 2008-104849 A | 5/2008 |
| JP | 2011-239863 A | 12/2011 |

OTHER PUBLICATIONS

International Search Report issued in International Application No. PCT/JP2012/059324 dated Jul. 10, 2012, with English Translation.

* cited by examiner

OPTICAL MEASURING SYSTEM

CROSS REFERENCE TO RELATED APPLICATIONS

This application is a U.S. national phase application of PCT International Patent Application Number PCT/JP2012/059324 filed on Apr. 5, 2012, the entire content of which is incorporated by reference.

TECHNICAL FIELD

The present invention relates to an optical measuring system for measuring living body internal information (measurement data) non-invasively using light, and, more specifically, relates to an optical measuring system of a multichannel type, having a plurality of light transmitting points for directing light into the living body and a plurality of light receiving points for receiving light that is emitted from the living body, for measuring information from within the living body for a plurality of channels, established for each combination of an individual light transmitting point and individual light receiving point.

The present invention is well-suited for medical instruments that measure brain function or that perform diagnostics of circulatory disturbances through measuring changes over time in the blood flow to the various portions of the brain, and measurements of changes in the supply of oxygen within the living body.

BACKGROUND ART

In recent years, in order to observe the state of cerebral activity, optical brain function imaging devices have been developed to perform measurements conveniently and non-invasively using light. In such brain function imaging devices, near infrared beams of three different wavelengths $\lambda 1$, $\lambda 2$, and $\lambda 3$ (for example, 780 nm, 805 nm, and 830 nm) are directed into the brain through light transmitting probes that are disposed on the head surface of the patient, and the strengths of the near infrared lights of the respective wavelengths $\lambda 1$, $\lambda 2$, and $\lambda 3$ emitted from the brain (received brightness information) $A(\lambda_1)$, $A(\lambda_2)$, and $A(\lambda_3)$ are detected through light receiving probes disposed on the head surface.

Given this, a system of equations, shown in the exemplary system of equations (1), (2), and (3), is created using, for example, the Modified Beer Lambert method, in order to solve for the integral, along the length of the optical path, of the oxyhemoglobin (oxyHb) within the cerebral blood flow, and the integral, along the length of the optical path, of the deoxyhemoglobin concentration (deoxyHb) (referencing, for example, non-Patent Citation 1) from the light receiving intensity information $A(\lambda_1)$, $A(\lambda_2)$, and $A(\lambda_3)$. Moreover, from the integral, along the length of the optical path, of the oxyhemoglobin concentration (oxyHb) and the integral, along the length of the optical path, of the deoxyhemoglobin concentration (deoxyHb), the integral, along the length of the optical path, of the total hemoglobin concentration ((oxyHb)+(deoxyHb)) is calculated.

$$A(\lambda_1) = E_O(\lambda_1) \times [\text{oxyHb}] + Ed(\lambda_1) \times [\text{deoxyHb}] \quad (1)$$

$$A(\lambda_2) = E_O(\lambda_2) \times [\text{oxyHB}] + Ed(\lambda_2) \times [\text{deoxyHb}] \quad (2)$$

$$A(\lambda_3) = E_O(\lambda_3) \times [\text{oxyHB}] + Ed(\lambda_3) \times [\text{deoxyHb}] \quad (3)$$

Note that $E_O(\lambda n)$ is a light absorption coefficient for the oxyhemoglobin for light at the wavelength of $\lambda m$, and $E_d(\lambda m)$ is a light absorption coefficient for deoxyhemoglobin for light of the wavelength $\lambda m$.

The relationship between the measurement location and the distance (the channel) between the light transmitting probe and the light receiving probe will be explained here. FIG. 11A is a cross-sectional diagram showing the relationship between the measurement location and a light transmitting probe and light receiving probe pair, where FIG. 11B is a plan view diagram of FIG. 11A.

The light transmitting probe 12 is pressed against a light transmitting point T on the head surface of the patient and the light receiving probe 13 is pressed against a light receiving point R on the head surface of the patient. Moreover, light is emitted from the light transmitting probe 12, and the light that is emitted from the head surface is received into the light receiving probe 13. Of the light that is emitted from the light transmitting point T on the head surface, that light that traverses a banana shape (a measuring region) arrives at the light receiving point R of the head surface. This makes it possible to obtain light reception brightness information $A(\lambda_1)$, $A(\lambda_2)$, and $A(\lambda_3)$ regarding the measurement location of the patient that is at a depth of L/2 that is one half of the distance of the line connecting the light transmitting point T to the light receiving point R through the shortest distance along the head surface of the patient, from, in particular, the midpoint M of the line L that connects the light transmitting point T and the light receiving point R of through the shortest distance along the head surface of the patient, within the measurement region.

Moreover, in this optical brain function imaging device, a near-infrared spectroscopic analyzer (referencing Patent Citation 1, for example), or the like is used in order to measure separately the oxyhemoglobin concentration integrated along the length of the optical path (oxyHb), the deoxyhemoglobin concentration integrated along the length of the optical path (deoxyHb), and total hemoglobin concentration integrated along the length of the optical path ((boxyHb)+(deoxyHb)) in relation to a plurality of measurement locations within the brain.

FIG. 12 is a block diagram illustrating one example of a schematic structure for a conventional near-infrared spectroscopic analyzer. Moreover, FIG. 13 is a perspective diagram illustrating one example of the external appearance of the near-infrared spectroscopic analyzer illustrated in FIG. 12. Note that for ease of understanding, the plurality of optical fibers for light transmission and plurality of optical fibers for light reception, and the like, are omitted.

The near-infrared spectroscopic analyzer 201 has a case 211 that is of a rectangular-solid shape (for example, 70 cm×100 cm×120 cm).

A light source driver 202 for emitting light, an photodetector 203 for detecting light, an A/D converter 5, a controller 21 for light transmission/reception, a controller 22 for analysis, and a memory 23 are provided within the case 211, and 16 light transmitting probes 12, 16 light receiving probes 13, 16 light transmission optical fibers 14, 16 light reception optical fibers 15, a display device 226, and a keyboard 227 are provided outside of the case 221.

The light source driver 202 is a light source for the transmission of light to the various light transmitting probes 12 depending on driving signals inputted from the light transmission and reception controller 21, and is, for example, semiconductor lasers LD1, LD2, and LD3, or the like, which are able to emit near-infrared light of, for example, three different wavelengths $\lambda_1$, $\lambda_2$, and $\lambda_3$.

The photodetector 203 is a detector, for example, a photoelectron multiplying tube, or the like, for detecting the respective near-infrared lights received by the individual light receiving probes 13, and outputting to the light transmission and reception controller 21 16 light reception signals (light reception brightness information) $A(\lambda_1)$, $A(\lambda_2)$, and $A(\lambda_3)$ through the A/D converters 5.

The light transmission optical fibers 14 and the light reception optical fibers 15 each have a cylindrical shape with respective diameters of 2 mm and lengths between 2 m and 10 m, and are able to transmit the near-infrared light in the axial direction thereof, where near infrared light that enters in from one end portion passes through the interior thereof to be emitted from the other end portion, and where near-infrared light that enters in from the other end portion passes through the interior thereof to be emitted from the one end portion.

Moreover, for a single light transmission optical fiber 14, a single light transmitting probe 12, and individual semiconductor lasers LD1, LD2, and LD3 of the light source driver 202, are connected to the end portions thereof, separated by a set length (between 2 m and 10 m). Moreover, for a single light reception optical fiber 15, a single light receiving probe 13 and a single photoelectron multiplier tube of the photodetector 203 are connected to the end portions thereof, separated by the set length (between 2 m and 10 m).

In this near-infrared spectroscopic analyzer 201, a holder 130 is used to cause the 16 light transmitting probes 12 and the 16 light receiving probes 13 to contact the head surface of the patient in a prescribed array. FIG. 14 is a plan view illustrating one example of a holder 130 into which the 16 light transmitting probes and the 16 light receiving probes have been inserted.

The light transmitting probes $12_{T1}$ through $12_{T16}$ and the light receiving probes $13_{R1}$ through $13_{R16}$ are disposed so as to alternate with four probes in the lateral direction and eight probes in the crosswise direction, with constant spacing between the light transmitting probes 12 and the light receiving probes 13, to obtain, from the head surface, light reception brightness information $A(\lambda_1)$, $A(\lambda_2)$, and $A(\lambda_3)$ for a specific depth from the head surface. Note that the spacing between probes is known as a "channel," where typically 30 mm is used for the channel, where, if the channel is 30 mm, then the light reception brightness information $A(\lambda_1)$, $A(\lambda_2)$, and $A(\lambda_3)$ for a depth of between about 15 mm and 20 mm from the midpoint of the channel is envisioned. That is, light reception brightness information $A(\lambda_1)$, $A(\lambda_2)$, and $A(\lambda_3)$ related to cerebral activity is obtained essentially corresponding to the position on the surface of the brain, at a position that is between 15 mm and 20 mm deep from the head surface.

Note that the various through holes are assigned different codes (T1, T2, . . . , R1, R2, . . . ) so as to identify the type of light transmitting probe $12_{T1}$ through $12_{T16}$ or light receiving probe $13_{R1}$ through $13_{R16}$ that is at each through hole of the holder 130, and the individual light transmitting probes $12_{T1}$ through $12_{T16}$ are also assigned respective unique codes (T1, T2, . . . ) and the individual light receiving probes $13_{R1}$ through $13_{R16}$ are also assigned respective unique codes (R1, R2, . . . ). As a result, the individual light transmitting probes $12_{T1}$ through $12_{T16}$ and the individual light receiving probes $13_{R1}$ through $13_{R16}$ are each inserted into the respective through holes with the corresponding codes.

Moreover, the curvature of the head surface of the patient will vary depending on gender, age, and individual differences. Thus, in order to enable easy compatibility even when there are differences in curvature of the head surface, a holder 130 is used wherein the holders for holding the light transmitting probes $12_{T1}$ through $12_{T16}$ and the light receiving probes $13_{R1}$ through $13_{R16}$ are disposed in a grid shape on the head surface, where the holders are connected together by connectors that exhibit flexibility, and wherein there is rotational variability of the connectors, rotating around the holders, within a prescribed angle (referencing, for example, Patent Citation 2).

Furthermore, in the location relationships between these 16 light transmitting probes $12_{T1}$ through $12_{T16}$ and these 16 light receiving probes $13_{R1}$ through $13_{R16}$ it is necessary to adjust the timing of illumination with light from the light transmitting probes 12 and the timing of reception of light by the light receiving probes 13 so that light which is emitted from only a single light transmitting probe 12 will be received by a single light receiving probe 13, without simultaneously receiving light emitted by a plurality of light transmitting probes 12. Because of this, a control table that indicates the timing for emitting light, by the light source driver 202, and timing for detecting light, by the photodetector 203, is stored in the memory 23.

The light transmission and reception controller 21 outputs, to the light source driver 202, a signal for driving the transmission of light to a single light transmitting probe at a prescribed time, based on the control table that is stored in the memory 23, and also detects, through the photodetector 23, the reception signal (light reception brightness information) for the light received by the light receiving probe 13. The result, when shown in a plan view as illustrated in FIG. 14, is the collection of a total of 52 (S1 through S52) light reception brightness information $A(\lambda_1)$, $A(\lambda_2)$, and $A(\lambda_3)$.

Given this, the analysis controller 22 uses the system of equations (1), (2), and (3), to calculate the integral of the oxyhemoglobin concentration along the length of the optical path (oxyHb), the integral of the deoxyhemoglobin concentration along the length of the optical path (deoxyHb), and the integral of the total hemoglobin concentration along the length of the optical path ((oxyHb)+(deoxyHb)) (measurement data) based on the total of 52 light reception brightness information $A(\lambda 1)$, $A(\lambda 2)$, and $A(\lambda 3)$.

PRIOR ART CITATIONS

Patent Citation

Patent Citation 1: Japanese Unexamined Patent Application Publication 2001-337033

Patent Citation 2: Japanese Unexamined Patent Application Publication 2002-143169

Non-Patent Citation

Non-Patent Citation 1: "Factors Affecting the Accuracy of Near-Infrared Spectroscopy Concentration Calculations for Focal Changes in Oxygenation Parameters," NeuroImage 18, 865-879, 2003

SUMMARY OF THE INVENTION

Problem Solved by the Present Invention

The size of the case 211 for the near-infrared spectroscopic analyzer 201, described above, is, for example, 70 cm×100 cm×120 cm, which is quite large. However, some patients undergo rehabilitation on a daily basis, in which case the location at which a patient undergoes rehabilitation may be the residence of the patient or may be a rehabilitation facility, or the like, where the provision of the near-infrared spectroscopic analyzer 201 in each individual home is essentially impossible from a perspective of both installation space and cost, and transporting the near-infrared spectroscopic analyzer 201 from the clinic to the rehabilitation center is extremely laborious.

Means for Solving the Problem

The inventors in this case have previously applied for a patent for an optical measuring system that is able to measure measurement data easily in a patient's home, or the like. In this optical measuring system, two different optical measuring devices are used depending on the circumstances: a main optical measuring device that is provided with, for example, 16 light transmitting probes, 16 light receiving probes, and a case (which measures, for example, 70 cm×100 cm×120 cm), and a mobile optical measuring device that is provided with 4 light transmitting probes, 4 light receiving probes, and a case (which measures, for example, 10 cm×10 cm×50 cm).

Given this, the expensive main optical measuring device is installed in a hospital, and the inexpensive mobile optical measuring device is disposed in the home of the patient, or the like. Furthermore, to enable observation of the measurement data of the patient at the patient's home, the rehabilitation facilities, or the like, the measurement data obtained by the inexpensive mobile optical measuring device is sent to, for example, an external PC, or the like, enabling the measurement data to be displayed on a display device of the external PC, or the like.

However, in the optical measuring system set point above, the mobile optical measuring device is moved to the patient, enabling measurement data for the patient to be obtained in a situation wherein rehabilitation is performed together with rigorous motion, but rehabilitation is seldom performed while a patient performs rigorous exercise, and actually when a patient is undergoing upper limb rehabilitation, usually the rehabilitation is performed using a puzzle or the like on a tabletop with the patient seated, in which case there is a problem in that the mobile optical measuring device, which has been moved to the patient, becomes an impediment.

Given this, the inventors in the present case researched optical measuring devices which enable the patient to undergo rehabilitation easily. In the case of rehabilitation being performed by the patient at the patient's home or a rehabilitation center, usually the rehabilitation, which uses puzzles, or the like, on a desktop with the patient seated in a chair, or the like, is performed by the individual, with the patient observing the details of the operation or the details of the rehabilitation. On the other hand, when the patient is receiving a rehabilitation status examination from a physician, or the like, then the patient performs actions based on instructions from the physician, or the like, and the physician, or the like, observes the details of the activities by the patient, the measurement data, and the like. That is, the locations at which rehabilitation is performed are not always the same locations, and while the rehabilitation is sometimes performed by the single individual, the rehabilitation is sometimes performed with two or more people. Consequently, a system was created that is carried easily and wherein, when rehabilitation is performed at the patient's home or in a rehabilitation center, can be placed on a tabletop and wherein an image of the patient himself/herself can be observed, while, on the other hand, if the patient is receiving an examination, the physician, or the like, is able to observe the image, because there is little need for the patient to observe the image. The result was the discovery of use of an optical meter for obtaining measurement data and a tablet controller that can be attached movably to the optical meter.

That is, the optical measuring system comprises a control device and an optical meter. The optical meter comprises a first case, a first controller, in the first case, configured to control light emitters for irradiating a patient with light, and light receivers for receiving light from the patient to obtain measurement data regarding a cerebral activity, and a first transmitter and receiver, in the first case, configured to transmit the measurement data to the control device. The control device comprises a second case removably attached to the first case, a display and input device on a surface of the second case, a second transmitter and receiver, in the second case, configured to receive the measurement data from the optical meter, and a second controller, in the second case, configured to control the display and input device to display the measurement data from the optical meter. The first case may be configured to be placed on a table or hung from the back of a chair. The second case may also be configured to be attached on a top face of the first case that is placed on the table.

The first transmitter and receiver and the second transmitter and receiver are provided to exchange data between the control device and the optical meter. Such data exchange can be performed in real-time through a wired or wireless communication.

Effects of the Invention

As described above, given the optical measuring system according the present invention, when rehabilitation is performed at the home of the patient or at a rehabilitation center, the second case is attached to the first case for use, enabling the patient to observe the image that is displayed on the display and input device. On the other hand, when the patient is examined, the second case is removed from the first case for use, enabling a person other than the patient to observe the image that is displayed on the display and input device. Moreover, because a tablet controller can be attached to the optical meter, it is carried easily.

Other Means for Solving the Problem, and Effects Thereof

Moreover, in the optical measuring system according to the present invention, the structure may be such that the first case can be placed on a table and also can be hung on the back of a chair, and the second case can be placed standing on the top face of the first case, which is placed on the table.

Here the "can be hung from the back of a chair" refers to the ability to be hung from the back rest of a chair, such as being hung from the back like a students backpack. Because of this, the size of the first case preferably is no less than 1000 cm$^3$ and no more than 3000 cm$^3$.

Given the optical measuring system according to the present invention, as described above, the optical meter can be hung from the back of a chair, enabling more of the tabletop to be available for use.

Moreover, in the optical measuring system according to the present invention, the tablet controller may have a one-person mode for displaying the details of the operations and the details of the rehabilitation on the display and input device, and a two-person mode for displaying the details of the operations and the measurement data on the display and input device.

Moreover, in the optical measuring system according to the present invention, the second case may be attached to the first case and the tablet controller may be placed in the one-person mode for use when the patient is observing the image that is displayed on the display and input device, and the second case may be removed from the first case and the tablet controller may be placed in the two-person mode for use when a person other than the patient is to observe the image that is displayed on the display and input device.

BRIEF DESCRIPTIONS OF THE DRAWINGS

FIG. 5 is a flowchart for explaining one example of a rehabilitation method when a patient undergoes rehabilitation in his/her own home, or the like.

FIG. 7 is a flowchart for explaining one example of a method by which a patient is examined by a physician, or the like.

EMBODIMENTS FOR CARRYING OUT THE INVENTION

An embodiment according to the present invention will be explained below with reference to the drawings. Note that the present invention is not limited to embodiments such as explained below, but rather includes a variety of forms within a range that does not deviate from the spirit or intent of the present invention.

First Embodiment

Figure 1:
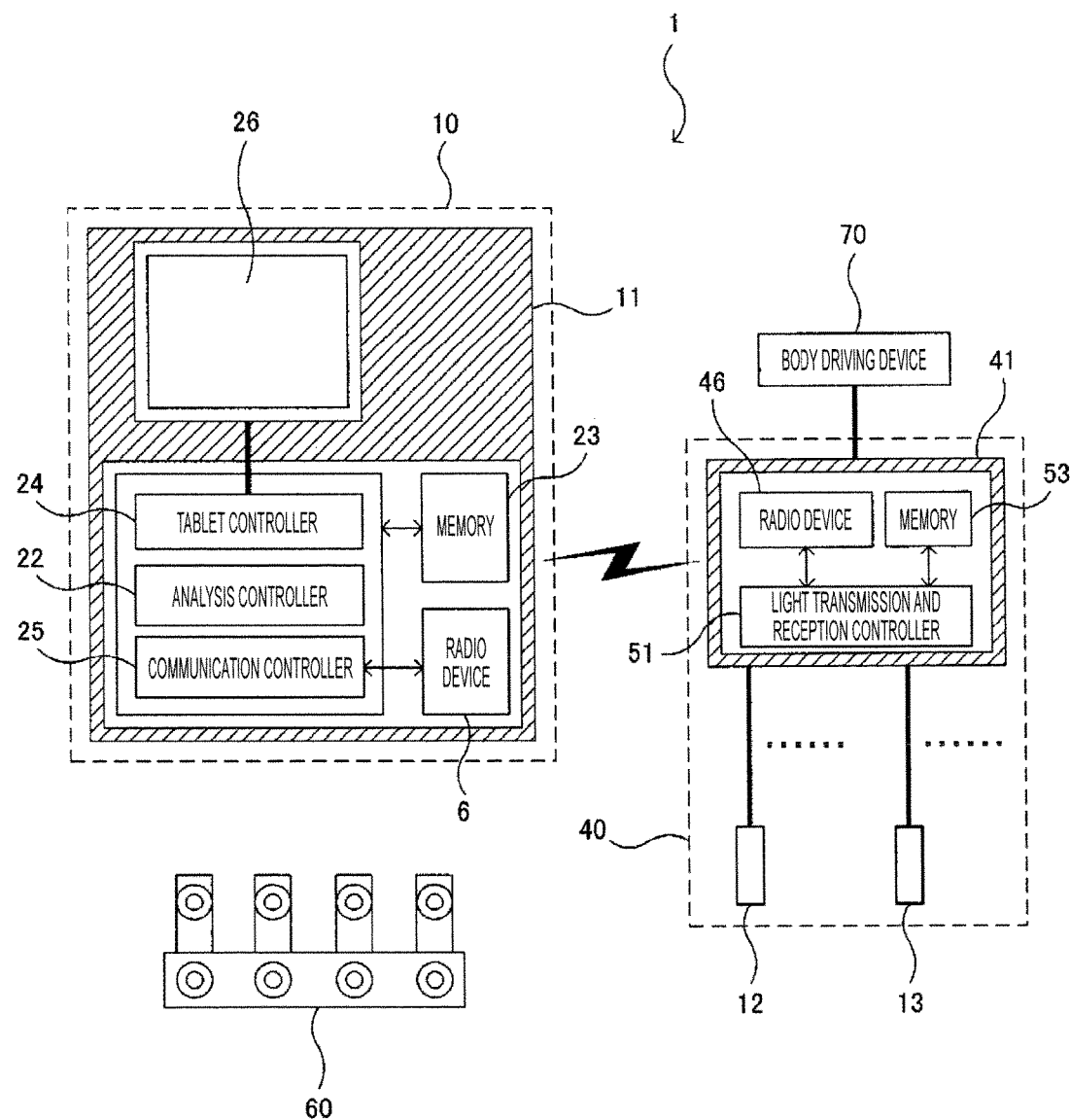
FIG. 1 is a block diagram illustrating a schematic structure of an optical measuring system that is a first embodiment according to the present invention.
Figure 2:
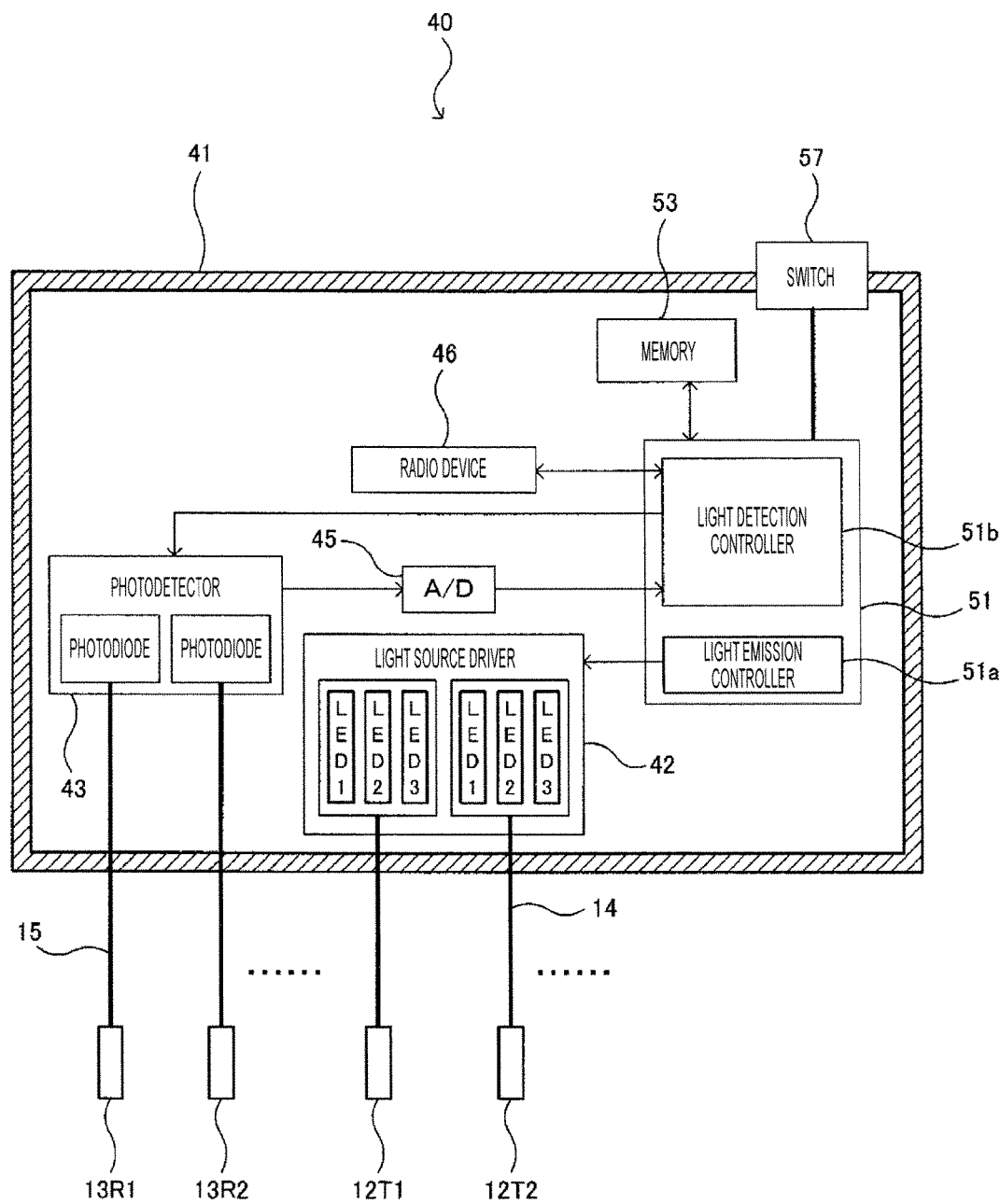
FIG. 2 is a block diagram illustrating details of the structure of the optical meter illustrated in FIG. 1.
Figure 3:
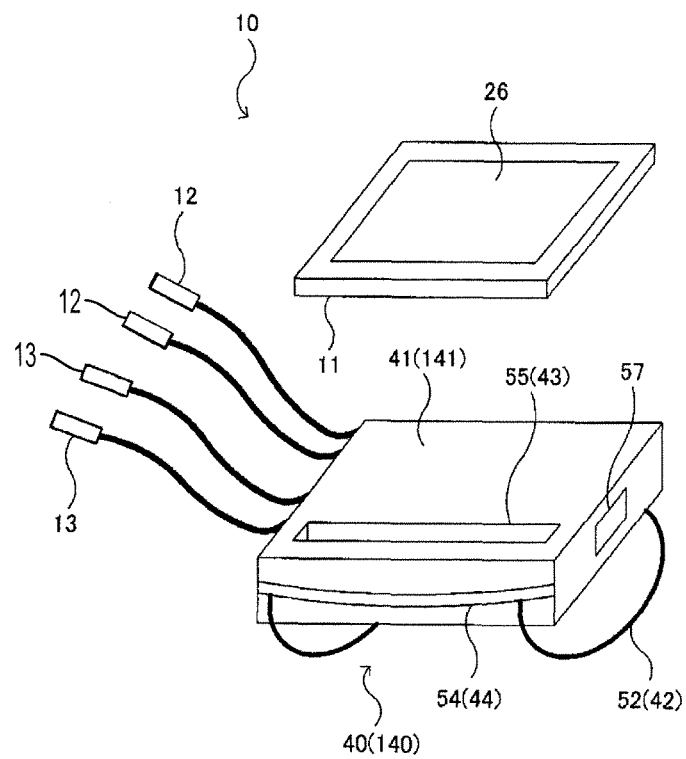
FIG. 3 is a perspective diagram illustrating one example of the exterior of the optical measuring system illustrated in FIG. 1.
Figure 4:
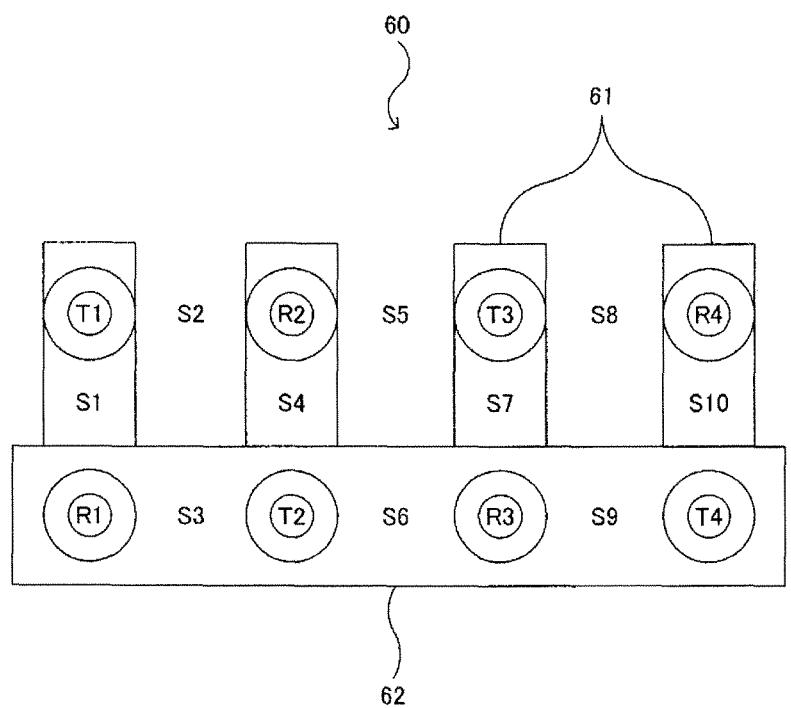
FIG. 4 is a plan view diagram illustrating one example of a comb-shaped holder into which four light transmitting probes and four light receiving probes are inserted.

FIG. 1 is a block diagram illustrating a schematic structure for an optical measuring system that is a first embodiment according to the present invention. Note that FIG. 2 is a block diagram illustrating details of the structure of the optical meter illustrated in FIG. 1. Additionally, FIG. 3 is a perspective diagram illustrating one example of an exterior view of the optical measuring system illustrated in FIG. 1. Furthermore, FIG. 4 is a plan view diagram illustrating one example of a comb-shaped holder wherein four light transmitting probes and four light receiving probes are inserted.

The optical measuring system 1 comprises an optical meter 40, a tablet control unit 10 that can be removably attached to the optical meter 40, a comb-shaped holder 60 that is disposed on the head of the patient, and a body driving device 70 that is disposed on a portion of the body of the patient. Note that identical references are assigned to those parts that are similar to those of the near-infrared spectroscopic analyzer 201.

With the present embodiment, the body driving device 70 is attached to the paralyzed left hand of the patient, and rehabilitation is performed wherein the patient completes a puzzle using the left-hand. Moreover, the patient undergoes rehabilitation at a rehabilitation center on a daily basis, and occasionally is examined by a physician at an examination center.

Note that there are no particular limitations on the body driving device 70 insofar as it is controlled based on signals outputted from the optical meter 40 or the tablet control unit 10. However in the present embodiment it is an artificial arm, shaped like a human arm, wherein the hand or fingers move like the real thing, and is operated based on an output signal.

The comb-shaped holder 60 is a comb shaped plate, wherein four branches 61, shaped in straight lines with a prescribed width (of, for example, 10 mm) are lined up in parallel with open spaces (of, for example, 30 mm) therebetween, and is provided with a single base trunk 62, shaped as a straight line, for connecting the ends of these branches 61 on one side.

Additionally, a cylindrical through hole is formed at the tip end portion at each of the branches 61, and cylindrical through holes are formed in positions in the base trunk 62 that are separated from those through holes by a channel length X (which is, for example, 30 mm). At this time, the through holes that are formed in the base trunk 62 are separated from each other by the channel length (for example, 30 mm).

Such a comb-shaped holder 60 is formed so that the patient is able to attach it to his/her head by himself/herself. Note that when performing measurements, each of the individual light transmitting probes $12_{T1}$ through $12_{T4}$ and each of the individual light receiving probes $13_{R1}$ through $13_{R4}$ are inserted into the inside of the through holes of the corresponding numbers.

The optical meter 40 has: a first case 41 of a rectangular solid shape (of, for example, 20 cm×30 cm×3 cm); an attaching portion 55 that is a recessed portion that is formed in the top face of the first case 41; two cloth belts 52 that are attached in parallel to the bottom face of the first case 41; and a round tab-shaped plastic grip 54 that is formed on the side face of the first case 41.

This enables the patient to place the bottom face of the first case 41 of the optical meter 40 onto a tabletop, and to use the two belts 52 to hang it from the back of a chair, and also enables the tablet control unit 10 to be attached to the optical meter 40, standing at a 90° angle, through inserting the bottom edge portion of the tablet control unit 10 into the attaching portion 55 of the first case 41 when it is placed on the tabletop.

A radio device (communication device, or transmitter and receiver) 46, for communicating wirelessly with the tablet control unit 10, a light transmission and reception controller 51, a memory 53 for storing the control table, a light source driver 42 for emitting light, a photodetector 43 for detecting light, and an A/D converter 45, are provided within the first case 41. Moreover, four light transmitting probes (light emitters) 12T1 through 12T4, four light receiving probes (light receivers) 13R1 through 13R4, four light transmission optical fibers 14, four light reception optical fibers 15, and a switch 57 for turning ON/OFF the power supply for the optical meter 40, are provided external to the first case 41.

The light source driver 42 is a light source for transmitting the respective lights of the individual light transmitting probes $12_{T1}$ through $12_{T4}$, through a driving signal that is inputted from the light transmission and reception controller 51, and is, for example, light-emitting diodes LED1, LED2, and LED3, or the like, that are able to emit near-infrared radiation of three different wavelengths $\lambda_1$, $\lambda_2$, and $\lambda_3$. Consequently, the first case 41 may be small, because these are light-emitting diodes LED1, LED2, and LED3.

The photodetector 43 is a detector for outputting, to the light transmission and reception controller 51, the four light reception signals (light reception brightness information) $A(\lambda_1)$, $A(\lambda_2)$, and $A(\lambda_3)$ through the A/D converter 45, through detecting the respective near-infrared lights received by the individual light receiving probes $13_{R1}$ through $13_{R4}$, such as, for example, photodiodes, or the like. Consequently, the first case 41 can be small, because these are photodiodes.

When the function performed by the light transmission and reception controller 51 is explained through division into blocks, it has a light-emission controller 51a for outputting a driving signal to the light source driver 42, and a light detection controller 51b for transmitting, through the radio device 46, the light reception signals (light reception brightness information) $A(\lambda_1)$, $A(\lambda_2)$, and $A(\lambda_3)$, through receiving the light reception signals from the light detectors 43.

Given this, the light-emission controller 51a, upon reception of a start signal from the tablet control unit 10, performs control for outputting, to the light source driver 42, signals, to the light transmitting probes $12_{T1}$ through $12_{T4}$, for transmitting light based on the control table stored in the memory 53. Moreover, the light-detection controller 51b, upon reception of a start signal from the tablet control unit 10, performs control so as to transmit, through the radio device 46, the light reception brightness information $A(\lambda_1)$, $A(\lambda_2)$, and $A(\lambda_3)$ from the light detector 43, based on the control table that is stored in the memory 53.

The tablet control unit 10 has a second case 11 that is a rectangular solid (of, for example, 20 cm×15 cm×5 cm), and a display with a touch panel (a display and input device) 26 that is formed on the top face of the second case 11.

The touch panel 26 is provided with, for example, a liquid crystal display panel for displaying an image, and a pressure detecting layer, made from a transparent electrode that is formed on top of the liquid crystal display panel, and a transparent protective layer that is formed on top of the pressure detecting layer.

The liquid crystal display panel is that which displays an image based on a display signal from the tablet controller 24. Moreover, the pressure detecting layer is a layer wherein a plurality of transparent electrode strips that are lined up in the vertical direction and a plurality of transparent electrode strips that are lined up in the horizontal direction are stacked together, where a point of intersection between a single transparent electrode and another single transparent electrode forms an individual switch. That is, this makes it possible to detect a position that has been pressed, through the application of pressure to a position on the surface of the transparent protective film. Moreover, the pressure detecting layer outputs, to the tablet controller 24, specified position information, which is the position to which pressure is applied.

The tablet controller 24 performs control so as to cause an image to be displayed on the touch panel 26, receive specified position information through a specific part of an image, displayed on the touch panel 26, being touched (pressed) by a person, and generate input signals. For example, when the power supply is turned ON, the tablet controller 24 displays, on the touch panel 26, an operating detail image. The operating detail image is, for example, buttons for selecting either a "one-person mode" or a "two-person mode," a start button for starting a measurement, an end button for ending a measurement, and the like. When "one-person mode" is selected, then a rehabilitation detail image is displayed. The rehabilitation detail image is, for example, a video of the detail of the operation performed by the patient. On the other hand, if "two-person mode" is selected, then the measurement data #1 through #10 will be displayed as trend graphs.

Upon reception of a start signal from the tablet controller 24, the communication controller 25 transmits a start signal to the light transmission and reception controller 51 of the optical meter 40 through the radio device 6, and performs control so as to receive the light reception brightness information $A(\lambda_1)$, $A(\lambda_2)$, and $A(\lambda_3)$, obtained from the light transmission and reception controller 51 of the light meter 40, and to store the light reception brightness information $A(\lambda_1)$, $A(\lambda_2)$, and $A(\lambda_3)$ in the memory 23.

The analysis controller 22 calculates, and stores in the memory 23, measurement data #1 through #10 that show the changes over time in the integral of the oxyhemoglobin concentration along the length of the optical path (oxyHb), the integral of the deoxyhemoglobin concentration along the length of the optical path (deoxyHb), and the integral of the total hemoglobin concentration along the length of the optical path ((oxyHb)+(deoxyHb)), from the transmitted optical brightnesses for each of the individual wavelengths (the absorption wavelength for the oxyhemoglobin, and the absorption wavelength for the deoxyhemoglobin) using the system of equations (1), (2), and (3), based on the light reception brightness information $A(\lambda_1)$, $A(\lambda_2)$, and $A(\lambda_3)$, that are stored in the memory 23.

The method for using the optical measuring system 1 will now be explained. In the optical measuring system 1, first either the "one-person mode" or the "two-person mode" is selected. The "one-person mode" is selected if, primarily, the patient is to perform the rehabilitation by himself/herself in the rehabilitation center. On the other hand, the "two-person mode" is selected if, primarily, the patient is to be examined by a physician or the like at the clinic.

(1) One-Person Mode

Figure 5:
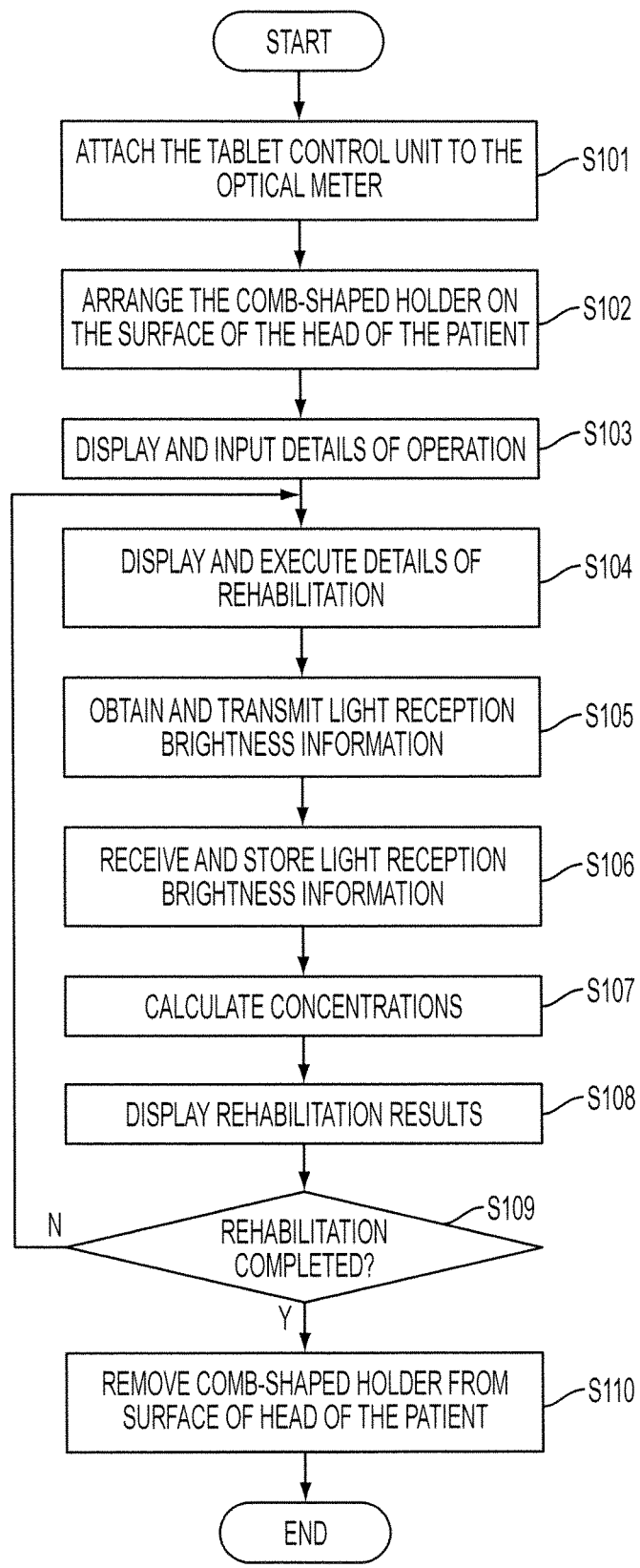
Figure 6:
FIG. 6 is an image of the one-person mode.

FIG. 5 is a flowchart for explaining one example of a method of rehabilitation when a patient performs rehabilitation in his/her home or in a rehabilitation center. Additionally, FIG. 6 is an image diagram for when the patient performs rehabilitation in a rehabilitation center (in the one-person mode).

First, in the procedure in Step S101, the optical meter 40 is placed on a table, and the tablet control unit 10 is attached, so as to stand in the attaching portion 55 of the first case 41.

That is, the patient, sitting in a seat, is able to observe the image that is displayed on the touch panel 26.

Next, in Step S102, the patient arranges the comb-shaped holder 60, the light transmitting probes $12_{T1}$ through $12_{T4}$, and the light receiving probes $13_{R1}$ through $13_{R4}$ on the surface of his/her own head.

Following this, in Step S103, the tablet controller 24 displays, on the touch panel 36, an image of the details of the operation. As a result, the patient uses the touch panel 26 to select the "one-person" mode, and touches the start button.

Following this, in Step S104, the tablet controller 24 causes an image of the detail of the rehabilitation to be displayed on the touch panel 26.

Given this, the patient performs the rehabilitation while observing the image that is displayed. Next, in Step S105, the light transmission and reception controller 51, through outputting a driving signal to the light source driver 42 and receiving a light reception signal from the photodetector 43, transmits the light reception signals (light reception brightness information) $A(\lambda_1)$, $A(\lambda_2)$, and $A(\lambda_3)$ through the radio device 46.

Following this, in Step S106, the communication controller 25 receives the light reception brightness information $A(\lambda_1)$, $A(\lambda_2)$, and $A(\lambda_3)$ through the radio device 6, and causes the light reception brightness information $A(\lambda_1)$, $A(\lambda_2)$, and $A(\lambda_3)$ to be stored in the memory 23.

Next, in Step S107, the analysis controller 22 calculates the integral of the oxyhemoglobin concentration along the length of the optical path (oxyHb), the integral of the deoxyhemoglobin concentration along the length of the optical path (deoxyHb), and the integral of the total hemoglobin concentration along the length of the optical path ((oxyHb)+(deoxyHb)), from the strengths of the transmitted light of the individual wavelengths, using the system of equations (1), (2), and (3), based on the light reception brightness information $A(\lambda_1)$, $A(\lambda_2)$, and $A(\lambda_3)$ stored in the memory 23.

Following this, in Step S108, the tablet controller 24 causes the rehabilitation result image to be displayed on the touch panel 26. The rehabilitation result image is, for example, that which shows the state of rehabilitation, and may be, for example, a score for the rehabilitation effects. This enables the patient to confirm that the rehabilitation is progressing as it should. That is, this becomes an incentive for rehabilitation.

Next, in Step S109, the patient evaluates whether or not the rehabilitation has been completed. If the evaluation is that the rehabilitation is to continue, then processing returns to the procedure of Step S104.

If, on the other hand, the evaluation is that the rehabilitation has been completed, then, in Step S110, the patient touches the End button, using the touch panel 26, and then removes the comb-shaped holder 60, the light transmitting probes $12_{T1}$ through $12_{T4}$, and the light receiving probes $13_{R1}$ through $13_{R4}$ from the surface of his/her head. The flowchart is thereby completed.

(2) Two-Person Mode

Figure 7:
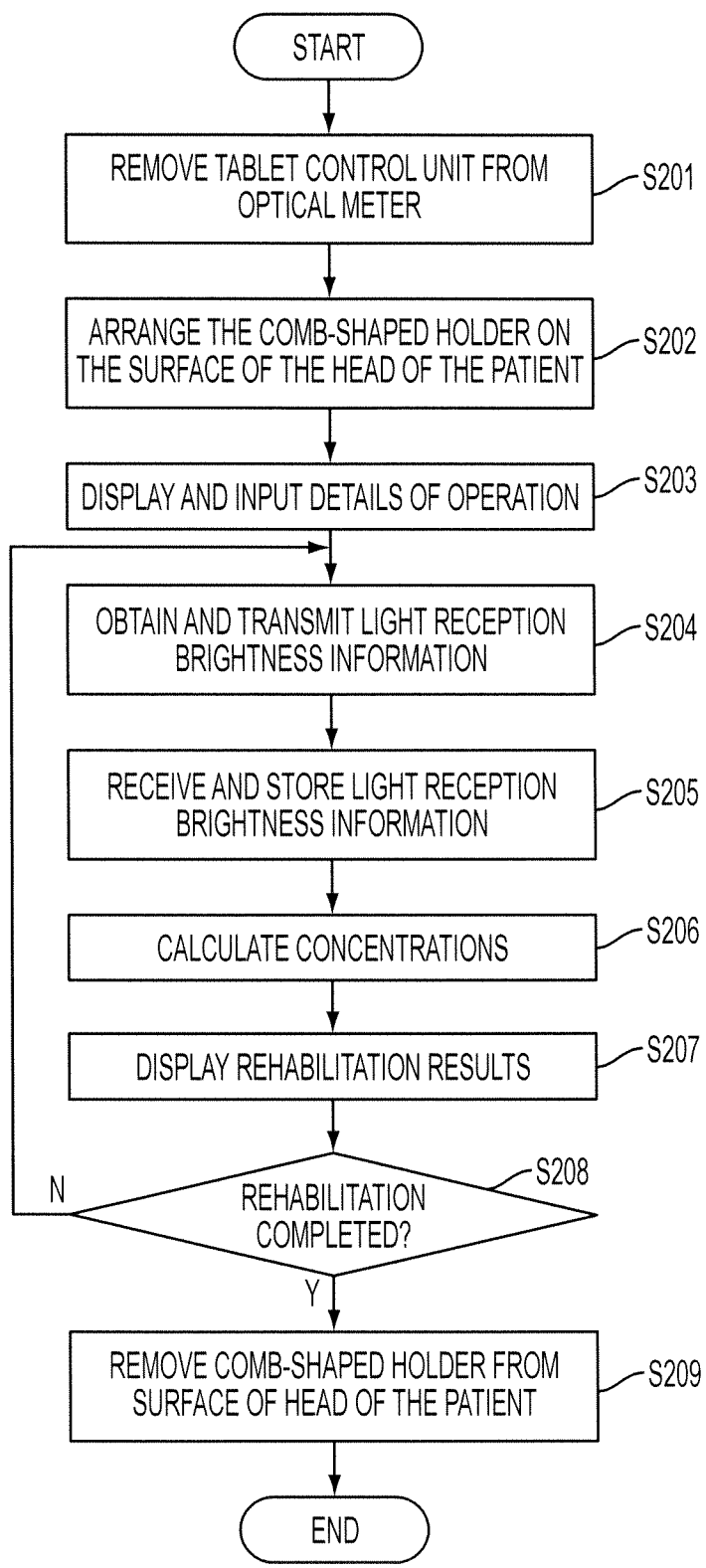
Figure 8:
FIG. 8 is an image of a two-person mode.

FIG. 7 is a flowchart for explaining one example of a method by which a patient is examined by a physician, or the like. Additionally, FIG. 8 is an image diagram for when a patient receives an examination by a physician, or the like (two-person mode).

First, in Step S201, the two belts 52 (referencing FIG. 3) are used to hang the optical meter 40 on the back of a chair, and the physician holds the tablet control unit 10, removed from the optical meter 40. That is, the physician is able to observe the image that is displayed on the touch panel 26, from a position that is away from the patient.

Following this, in Step S202, the physician arranges the comb-shaped holder 60, the light transmitting probes $12_{T1}$ through $12_{T4}$, and the light receiving probes $13_{R1}$ through $13_{R4}$ on the surface of the head of the patient, who is seated in a chair.

Next, in Step S203, the tablet controller 24 causes an image of the details of the operation to be displayed on the touch panel 26. Given this, the physician uses the touch panel 26 to select the "Two-Person Mode," and touches the Start button.

Next, in Step S204, the light transmission and reception controller 51, through outputting a driving signal to the light source driver 42 and receiving a light reception signal from the photodetector 43, transmits the light reception signals (light reception brightness information) $A(\lambda_1)$, $A(\lambda_2)$, and $A(\lambda_3)$ through the radio device 46. At this time, the patient undergoes rehabilitation in response to instructions from the physician.

Following this, in Step S205, the communication controller 25 receives the light reception brightness information $A(\lambda_1)$, $A(\lambda_2)$, and $A(\lambda_3)$ through the radio device 6, and causes the light reception brightness information $A(\lambda_1)$, $A(\lambda_2)$, and $A(\lambda_3)$ to be stored in the memory 23.

Next, in Step S206, the analysis controller 22 calculates the integral of the oxyhemoglobin concentration along the length of the optical path (oxyHb), the integral of the deoxyhemoglobin concentration along the length of the optical path (deoxyHb), and the integral of the total hemoglobin concentration along the length of the optical path ((oxyHb)+(deoxyHb)), from the strengths of the transmitted light of the individual wavelengths, using the system of equations (1), (2), and (3), based on the light reception brightness information $A(\lambda_1)$, $A(\lambda_2)$, and $A(\lambda_3)$ stored in the memory 23.

Following this, in Step S207, the tablet controller 24 displays the measurement data on the touch panel 26. As a result, the physician is able to decide whether or not to change the approach to the measurements.

Next, in Step S208, the physician evaluates whether or not the rehabilitation has been completed. If the evaluation is that the rehabilitation is to continue, then processing returns to the procedure of Step S204.

If, on the other hand, the evaluation is that the rehabilitation has been completed, then, in Step S209, the physician touches the End button, using the touch panel 26, and then the patient removes the comb-shaped holder 60, the light transmitting probes $12_{T1}$ through $12_{T4}$, and the light receiving probes $13_{R1}$ through $13_{R4}$ from the surface of his/her head. The flowchart is thereby completed.

As described above, given the optical measuring system 1 according to the present invention, if the patient is undergoing rehabilitation in his/her own home or in a rehabilitation center, the second case 11 is attached to the first case 41 for use, enabling the patient to observe the images that are displayed on the touch panel 26. On the other hand, if a physician is performing an examination at a clinic, the second case 11 is removed from the first case 41 for use, enabling the physician to observe the images that are displayed on the touch panel 26. Furthermore, the tablet control unit 10 can be attached to the optical meter 40, enabling it to be carried easily.

Second Embodiment

Figure 9:
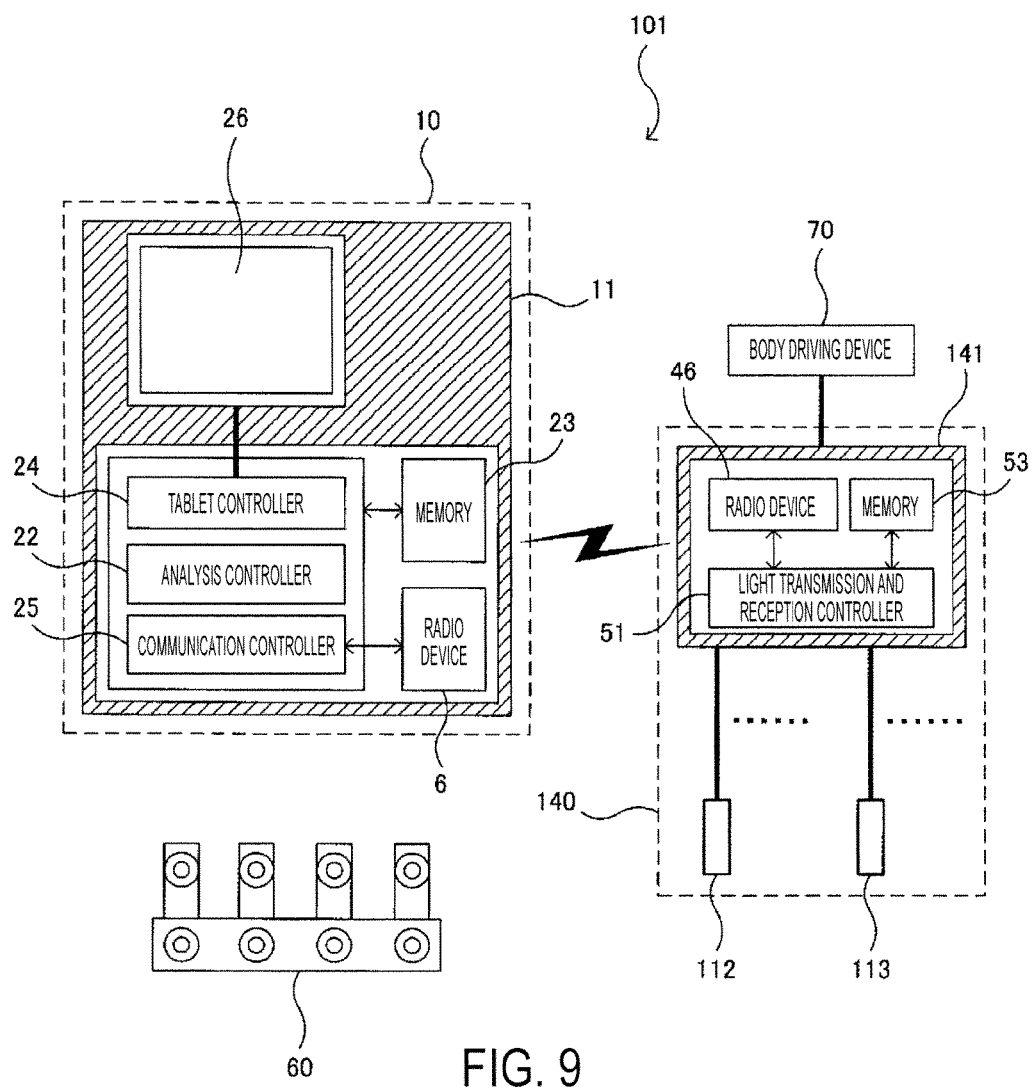
FIG. 9 is a block diagram illustrating a schematic structure of an optical measuring system that is a second embodiment according to the present invention.
Figure 10:
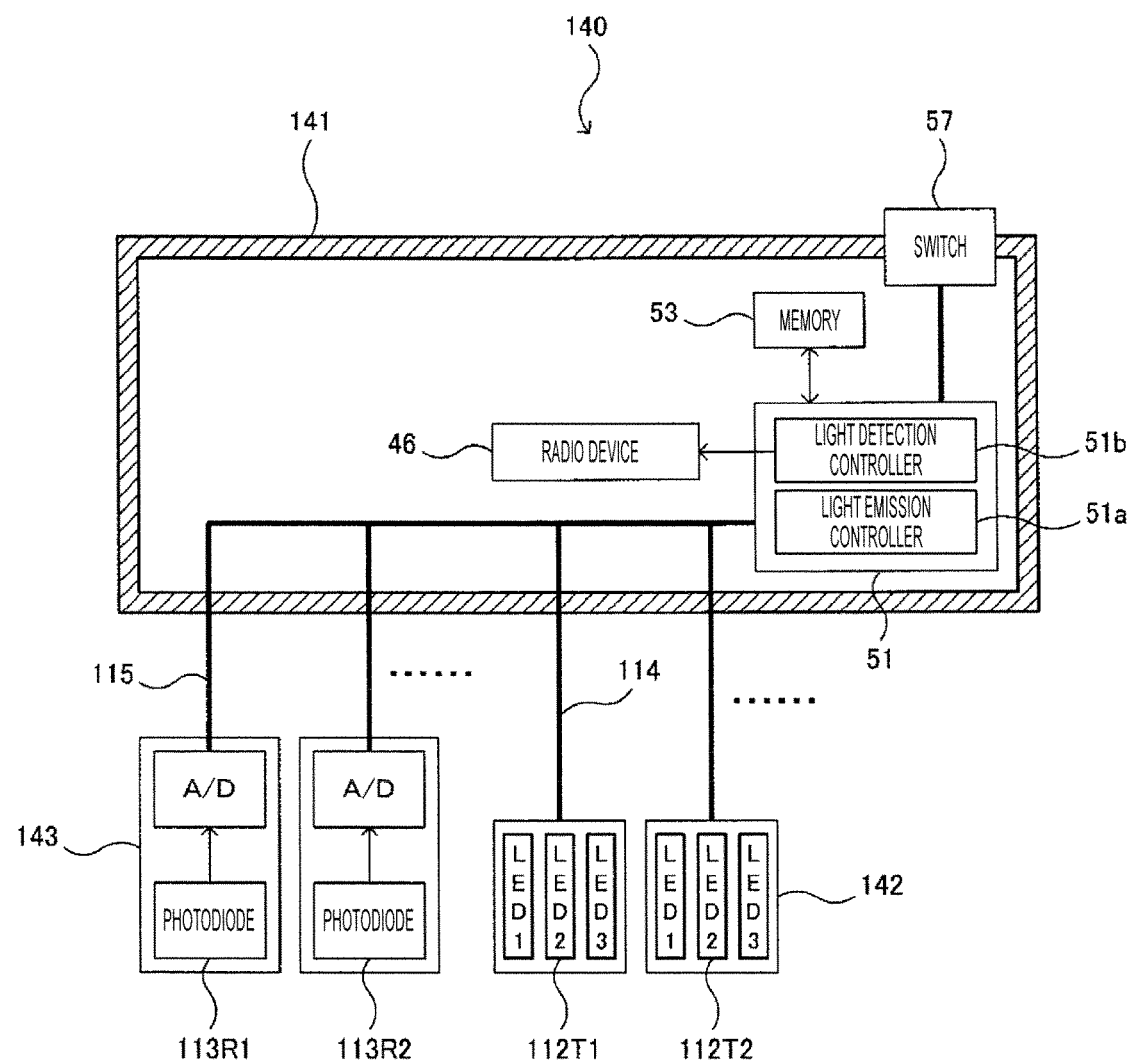
FIG. 10 is a block diagram illustrating details of the structure of the optical meter illustrated in FIG. 9.
Figure 11A:
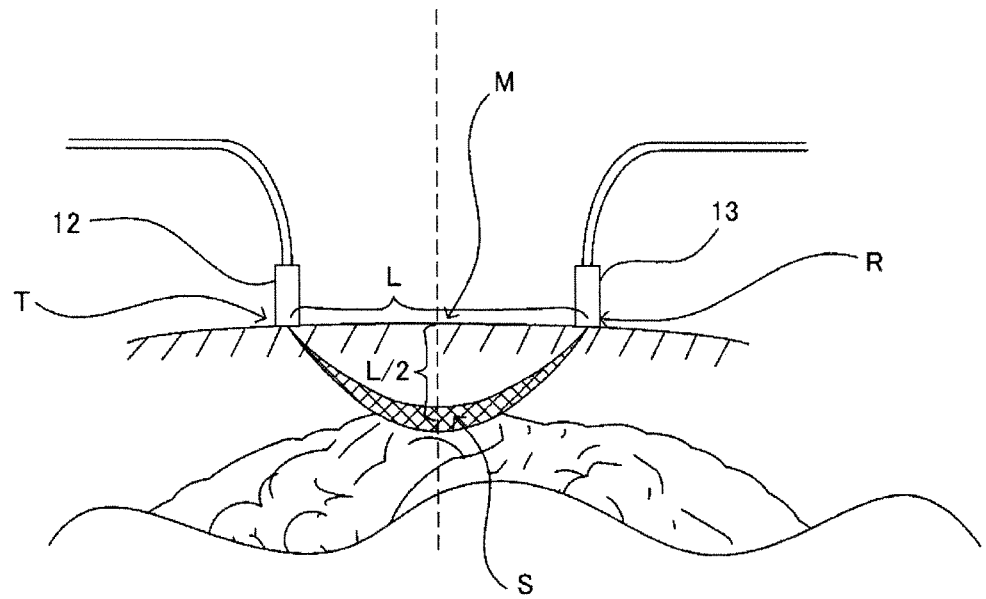
FIGS. 11A and 11B are diagrams illustrating the relationships between the light transmitting probe and light receiving probe pair and the measurement location.
Figure 11B:
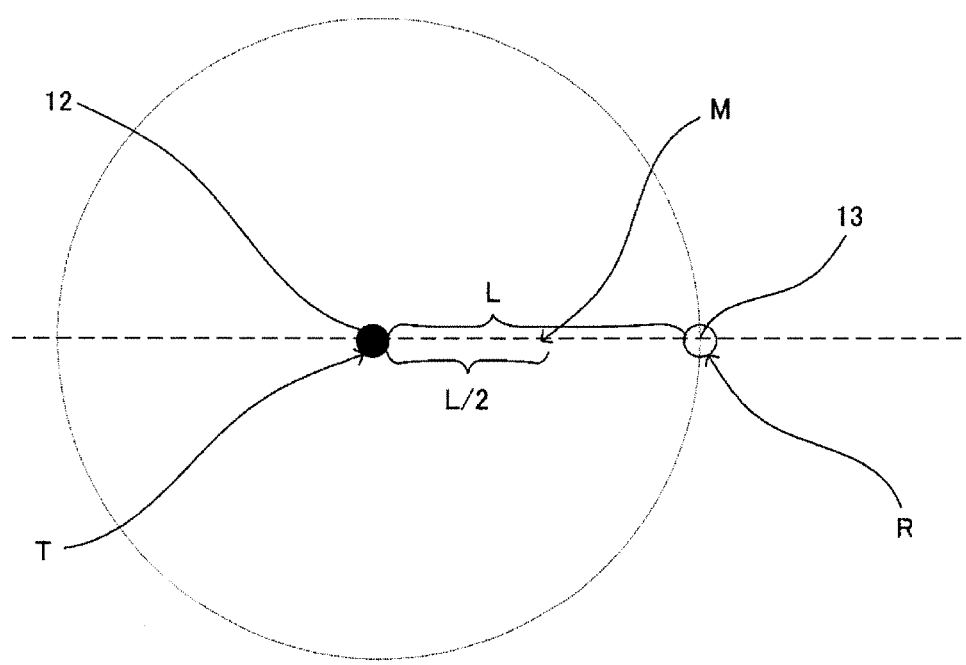
Figure 12:
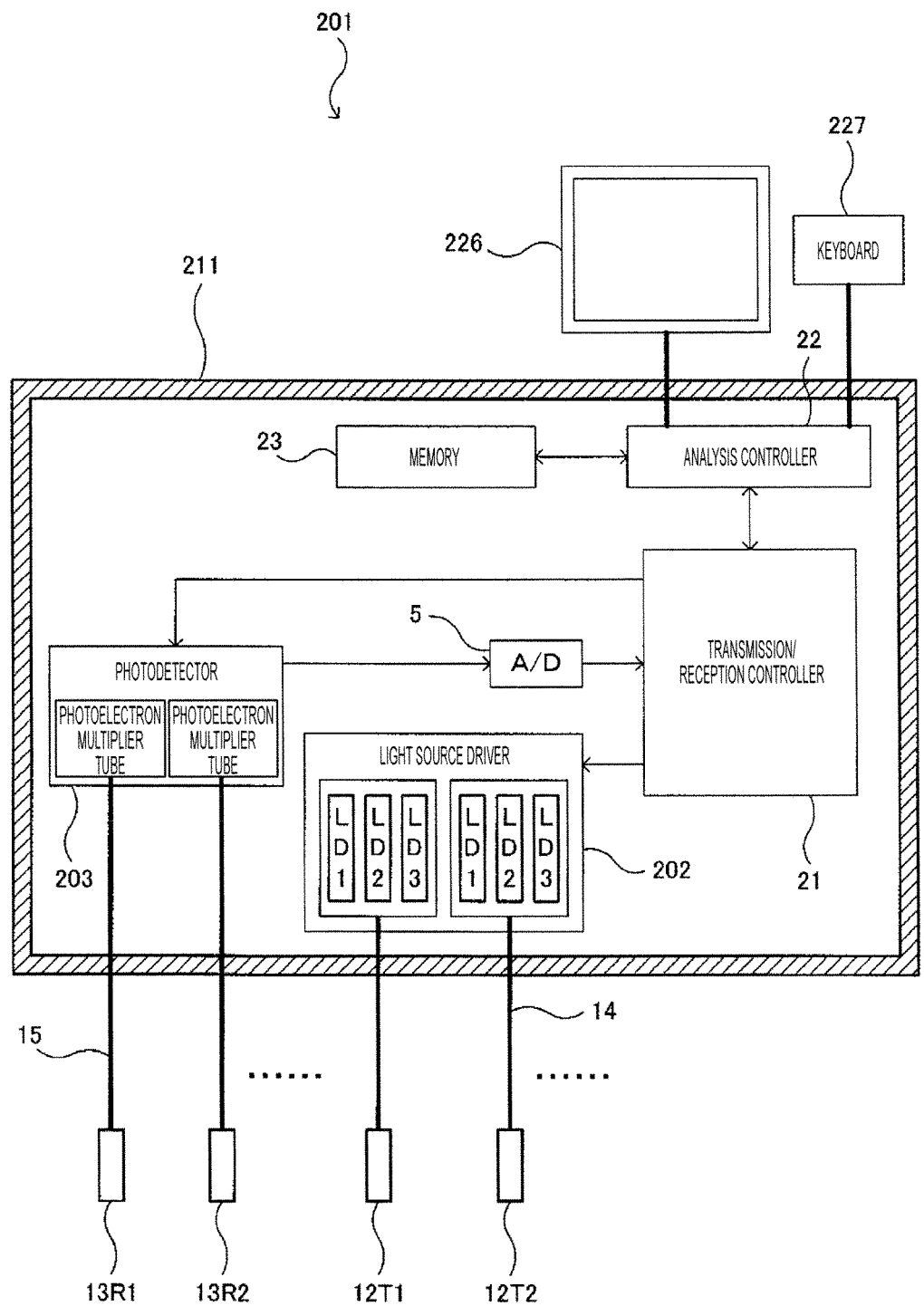
FIG. 12 is a block diagram illustrating one example of a schematic structure for a conventional near-infrared spectroscopic analyzer.
Figure 13:
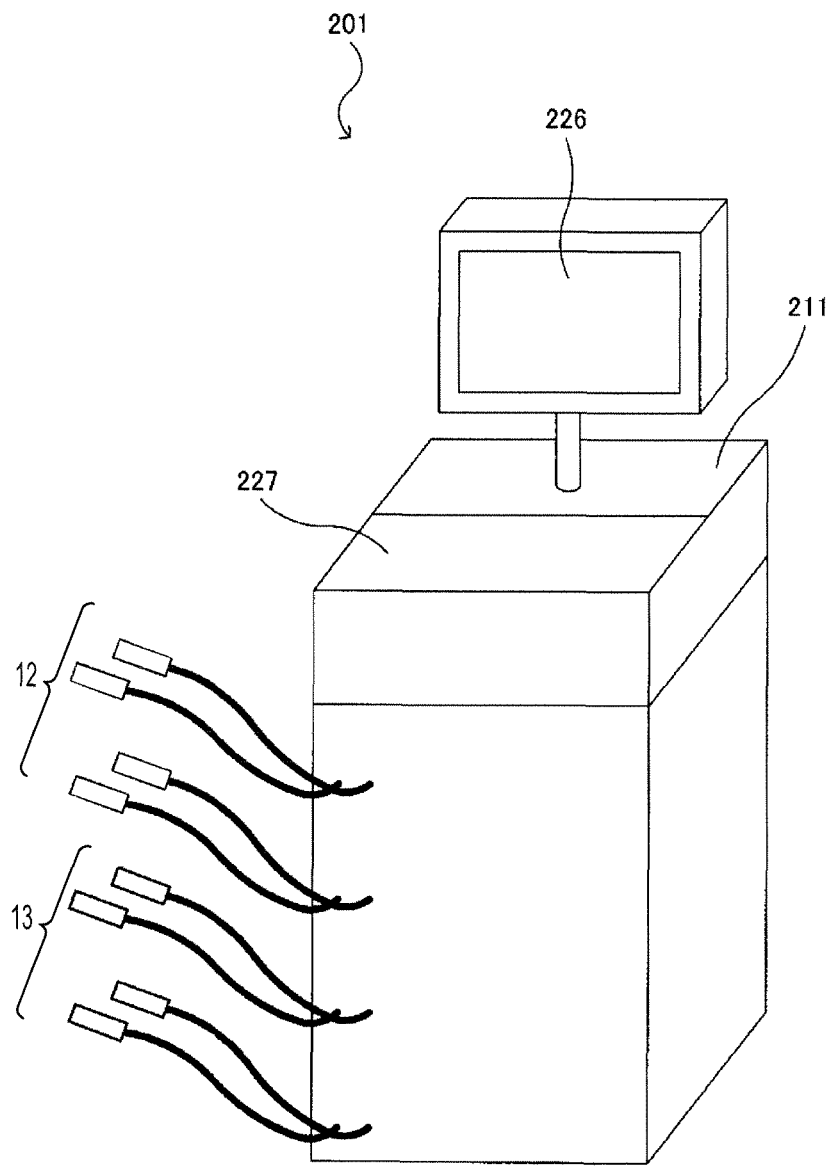
FIG. 13 is a perspective diagram illustrating one example of an exterior view of the near-infrared spectroscopic analyzer illustrated in FIG. 12.
Figure 14:
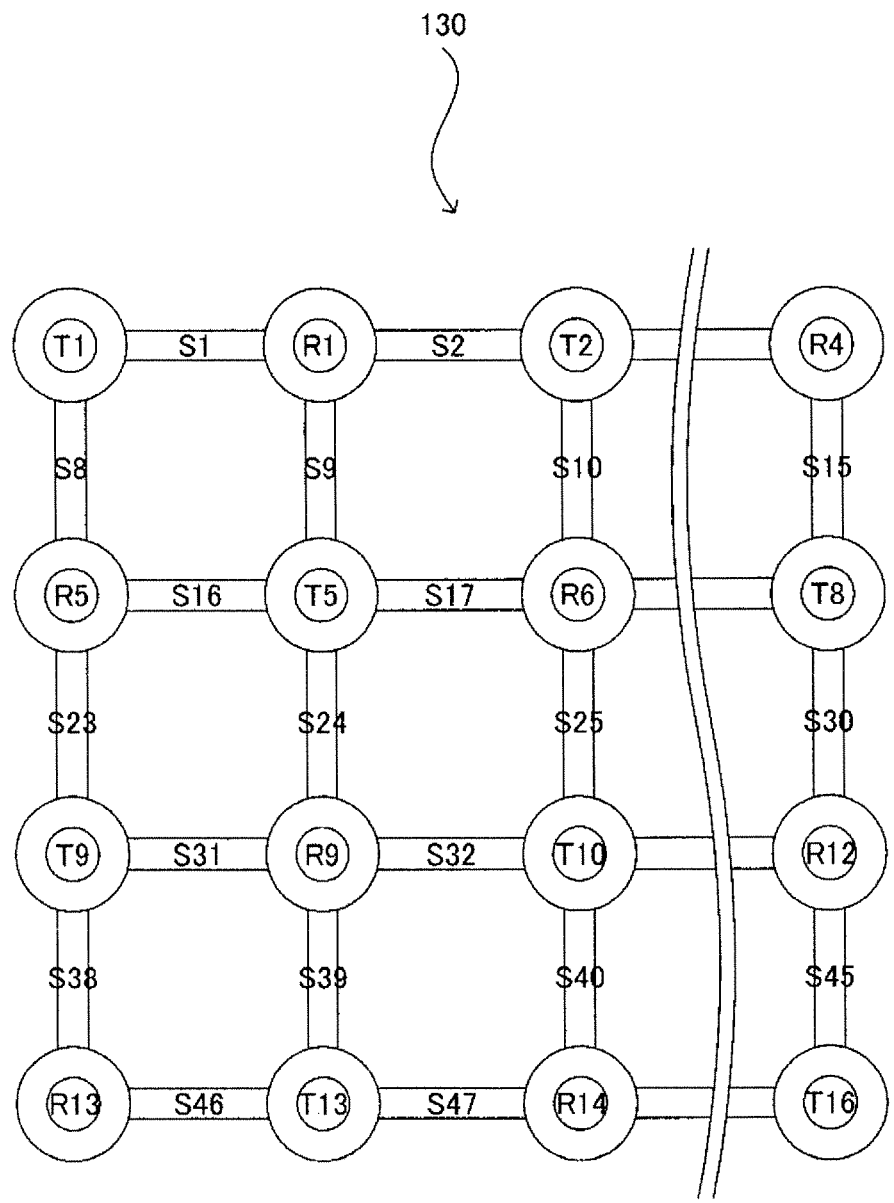
FIG. 14 is a plan view diagram of one example of a holder wherein light transmitting probes and light receiving probes are inserted.

FIG. 9 is a block diagram illustrating a schematic structure for an optical measuring system that is a second embodiment according to the present invention. Note that FIG. 10 is a block diagram illustrating details of the structure of the optical meter illustrated in FIG. 9.

The optical measuring system 101 comprises an optical meter 140, a tablet control unit 10 that can be removably attached to the optical meter 140, a comb-shaped holder 60 that is disposed on the head of the patient, and a body driving device 70 that is disposed on a portion of the body of the patient. Note that those parts that are identical to those in the optical measuring system 1 are assigned identical references.

The optical meter 140 has: a first case 141 of a rectangular solid shape (of, for example, 20 cm×30 cm×3 cm); an attaching portion 43 that is a recessed portion that is formed in the top face of the first case 141; two cloth belts 42 that are attached in parallel to the bottom face of the first case 141; and a round tab-shaped plastic grip 44 that is formed on the side face of the first case 141 (referencing FIG. 3).

A radio device (communication device, or transmitter and receiver) 46, for communicating wirelessly with the tablet control unit 10, a light transmission and reception controller 51, and a memory 53 for storing the control table are provided within the first case 141. Moreover, four light transmitting probes (light emitters) 112T1 through 121T4, four light receiving probes (light receivers) 113R1 through 113R4, four light transmission electrical cables 114, four light reception electrical cables 115, and a switch 57 for turning ON/OFF the power supply for the light meter 140, are provided external to the first case 141.

A single light transmitting probe 112 has a single light source driver 142 (light-emitting diodes LED1, LED2, and LED3), where a single light transmission electric cable 114 has a tube shape, with a diameter of 2 mm and a length between 2 m and 10 m, where an electric signal can be transmitted in the axial direction, where the single light transmitting probe 112 and the light-emission controller 51a are connected on both ends so as to be separated by a specific distance (between 2 m and 10 m).

Moreover, a single light receiving probe 113 has a single photodetector 143 (photodiode), where a single light reception electric cable 115 has a tube shape, with a diameter of 2 mm and a length between 2 m and 10 m, where an electric signal can be transmitted in the axial direction, where the single light reception probe 113 and the light-detection controller 51b are connected on both ends so as to be separated by a specific distance (between 2 m and 10 m).

As described above, given the optical measuring system 101 according to the present invention, if the patient is undergoing rehabilitation in his/her own home or in a rehabilitation center, the second case 11 is attached to the first case 141 for use, enabling the patient to observe the images that are displayed on the touch panel 26. On the other hand, if a physician is performing an examination at a clinic, the second case 11 is removed from the first case 141 for use, enabling the physician to observe the images that are displayed on the touch panel 26. Furthermore, the tablet control unit 10 can be attached to the optical meter 140, enabling it to be carried easily.

Other Embodiments

While in the optical measuring system 1 set forth above, a structure was illustrated wherein the optical meter 40 was provided with four light transmitting probes $12_{T1}$ through $12_{T4}$ and four light receiving probes $13_{R1}$ through $13_{R4}$, it may instead be provided with eight light transmitting probes and eight light receiving probes, or structured through the provision of eight light transmitting probes and four light receiving probes.

INDUSTRIAL APPLICABILITY

The present invention can be used in, for example, an optical measuring system for acquiring information from within a living body through directing light into the interior of the living body.

EXPLANATION OF CODES

1: Optical Measuring System
6: Radio Device (Communication Device)
10: Tablet Control Unit
11: Second Case
12: Light Transmitting Probe (Light Transmitting Means)
13: Light Receiving Probe (Light Receiving Means)
14: Light Transmission Optical Fiber
15: Light Reception Optical Fiber
22: Analysis Controller
24: Tablet Controller
26: Touch Panel (Display and Input Device)
40: Optical Meter
41: First Case
42: Light Source Driver
43: Photodetector
46: Radio Device (Communication Device)
51: Light Transmission and Reception Controller (Optical Meter Controller)
60: Comb-Shaped Holder

The invention claimed is:
1. An optical measuring system comprising:
an optical meter;
a control device being detachably mounted on the optical meter, wherein
the optical meter comprises:
    an attachment portion configured to support the control device when the control device is detachably mounted on the optical meter;
    a first controller configured to generate a driving signal to control light emitters for irradiating a patient with light and to control light receivers for receiving light from the patient, and configured to obtain measurement data regarding a cerebral activity; and
    a first transmitter and receiver configured to transmit the measurement data to the control device, and
the control device comprises:
    a display;
    a second transmitter and receiver configured to receive the measurement data transmitted from the optical meter; and
    a second controller configured to control the display to:
        display the measurement data from the optical meter when the control device is detached from the attachment portion of the optical meter, and
        display details of rehabilitation when the control device is mounted on the attachment portion of the optical meter.
2. The optical measuring system according to claim 1, wherein the control device has:
    a one-person mode for displaying details of a first operation and the details of rehabilitation on the display, and
    a two-person mode for displaying details of a second operation and the measurement data on the display.

3. The optical measuring system according to claim 2, wherein:
- when the control device is mounted on the optical meter, the control device operates in the one-person mode and allows the patient to observe a first image displayed on the display, and
- when the control device is detached from the optical meter, the control device operates in the two-person mode and allows an individual other than the patient to observe a second image displayed on the display.

4. The optical measuring system according to claim 1, wherein the optical meter is configured to be placed on a table or hung from a back of a chair.

5. The optical measuring system according to claim 4, wherein the control device is configured to be attached on a top face of the optical meter that is placed on the table.

6. The optical measuring system according to claim 1, further comprising a comb-shaped holder configured to hold the light emitters and the light receivers on a head of the patient.

7. The optical measuring system according to claim 1, further comprising an input device.

8. The optical measuring system according to claim 1, wherein the control device controls the display to further display at least one or more of a rehabilitation state, rehabilitation result, and a rehabilitation score.

* * * * *